United States Patent [19]

Spivack

[11] 4,069,200
[45] Jan. 17, 1978

[54] 2,3,5-TRIALKYL-4-HYDROXYBENZYL-PHOSPHONATES AND PHOSPHINATES

[75] Inventor: John D. Spivack, Spring Valley, N.Y.

[73] Assignee: Ciba-Geigy Corporation, Ardsley, N.Y.

[21] Appl. No.: 668,357

[22] Filed: Mar. 19, 1976

Related U.S. Application Data

[60] Division of Ser. No. 492,089, July 26, 1974, Pat. No. 3,962,377, which is a continuation-in-part of Ser. No. 400,601, Sept. 25, 1973, abandoned.

[51] Int. Cl.$^2$ .......................... C08K 5/36; C08K 5/53
[52] U.S. Cl. ..................... 260/45.85 S; 260/45.8 NT; 260/45.95 D; 260/953
[58] Field of Search ................................ 260/45.95 D

[56] References Cited

U.S. PATENT DOCUMENTS

| | | | |
|---|---|---|---|
| 3,006,945 | 10/1961 | Goddard et al. | 260/953 |
| 3,280,070 | 10/1966 | Di Battista et al. | 260/45.95 D |
| 3,376,258 | 4/1968 | Gysling et al. | 260/45.95 D |
| 3,502,613 | 3/1970 | Berger | 260/45.95 D |
| 3,644,279 | 2/1972 | Mathis et al. | 260/45.8 N |
| 3,655,614 | 4/1972 | Spivack | 260/45.95 D |
| 3,767,735 | 10/1973 | Fenyes et al. | 260/45.95 D |
| 3,951,912 | 4/1976 | Susi | 260/45.85 B |
| 3,962,376 | 6/1976 | Spivack et al. | 260/45.95 D |

*Primary Examiner*—Donald E. Czaja
*Assistant Examiner*—R. A. White
*Attorney, Agent, or Firm*—Luther A. R. Hall

[57] ABSTRACT

The compounds are trialkylsubstituted hydroxybenzyl-phosphonates and phosphinates having the formula

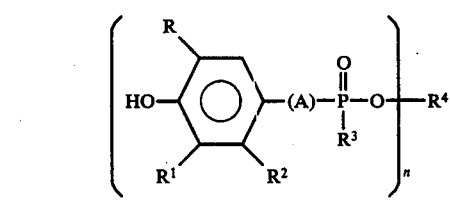

or

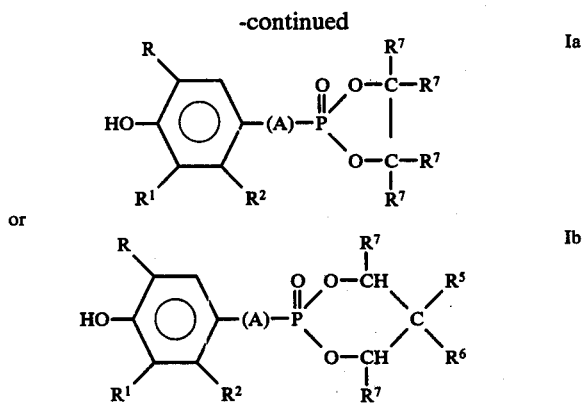

wherein R, $R^1$ and $R^2$ are independently lower alkyl or cycloalkyl groups, $R^3$ is alkyl, alkyl substituted with one halogen atom, phenyl, phenyl substituted with alkyl groups, alkoxy, alkoxy substituted with one halogen group, phenoxy, phenoxy substituted with alkyl groups, alkylthioethoxy, alkylpolyoxyalkylenoxy, $R^4$ is alkyl, alkylsubstituted with one halogen atom, cycloalkyl, phenyl, phenyl substituted with alkyl groups alkylthioethyl, thiobis-alkylene, alkyleneoxyalkylene, polyoxyalkylene, alkylpolyoxyalkylene, alkylene, polyvalent cyclic or acyclic hydrocarbon radical, $R^5$ and $R^6$ are independently hydrogen, alkyl of 1 to 12 carbon atoms, $R^6$ may also be the group Ic

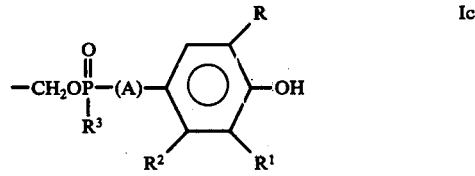

or together $R^5$ and $R^6$ represent the group Id

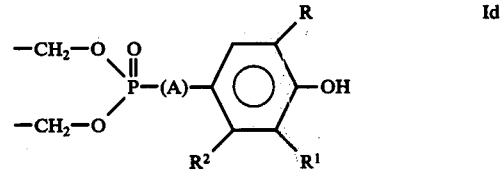

$R^7$ is hydrogen, alkyl or phenyl, A is lower alkylene and n is 1 to 4.

These compounds are usually prepared by reacting the trialkylsubstituted hydroxybenzyl or hydroxyphenylalkyl halide with the appropriate trialkyl or triaryl phosphite or appropriate substituted phosphonite.

The compounds are useful as stabilizers of organic materials subject to oxidative, thermal and photochemical degradation.

7 Claims, No Drawings

2,3,5-TRIALKYL-4-HYDROXYBENZYLPHOS-PHONATES AND PHOSPHINATES

This is a divisional of application Ser. No. 492,089 filed on July 26, 1974, now U.S. Pat. No. 3,962,377, which was a continuation-in-part of Ser. No. 400,601 filed on Sept. 25, 1973, now abandoned.

DETAILED DISCLOSURE

This invention pertains to trialkylsubstituted hydroxyphenylalkane phosphonates and phosphinates and to organic materials normally subject to oxidative, thermal and UV light deterioration stabilized with said phosphonates and phosphinates. More specifically, the compounds of this invention are those having the formula

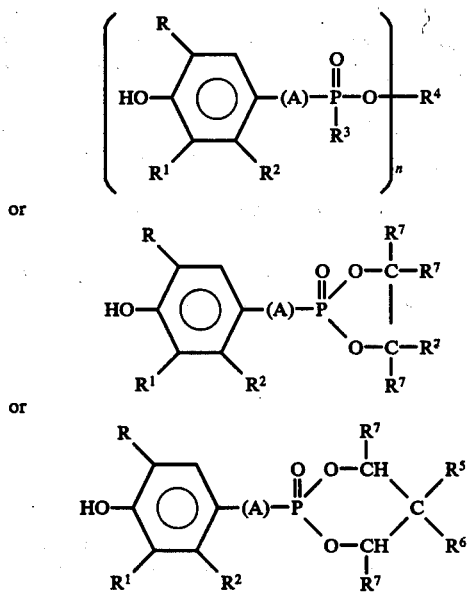

wherein

R, $R^1$ and $R^2$ are independently lower alkyl of 1 to 8 carbons, cycloalkyl of 5 or 6 carbons, provided that there are at most 2 cycloalkyl groups present or $R^1$ and $R^2$ together are a butylene chain which, together with the phenyl ring, form a tetrahydronaphthyl group, $R^3$ is alkyl of 1 to 24 carbon atoms, alkyl of 1 to 24 carbon atoms substituted by one halogen atom, phenyl, phenyl substituted with alkyl groups, said alkyl groups having 1 to 18 carbon atoms, alkoxy of 1 to 24 carbon atoms, alkoxy of 1 to 24 carbon atoms substituted with one halogen atom, phenoxy, phenoxy substituted with alkyl groups, said alkyl groups having 1 to 18 carbon atoms, alkylthioethoxy of 5 to 27 atoms in the chain or alkylpolyoxyalkyleneoxy of 5 to 28 atoms in the chain, $R^4$ is alkyl of 1 to 24 carbon atoms, alkyl of 1 to 24 carbon atoms substituted by one halogen atom, cycloalkyl of 5 to 6 carbon atoms, phenyl, phenyl substituted with alkyl groups, said alkyl groups having 1 to 18 carbon atoms, alkylthioethyl of 4 to 27 atoms in the chain, thiobisalkylene of 5 to 9 atoms in the chain, alkyleneoxyalkylene of 5 to 9 atoms in the chain, polyoxyalkylene of 8 to 101 atoms, alkylpolyoxyalkylene of 4 to 27 atoms in the chain, alkylene of 2 to 12 carbon atoms or a polyvalent acyclic or cyclic hydrocarbon radical of 3 to 10 carbon atoms, $R^5$ and $R^6$ are independently hydrogen, alkyl of 1 to 12 carbon atoms, the group having the formula Ic

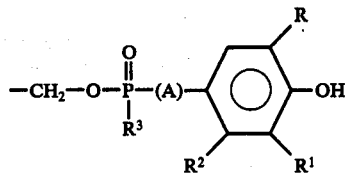

provided that only one of $R^5$ and $R^6$ can be the group of formula Ic or $R^5$ and $R^6$ together represent the group having the formula Id

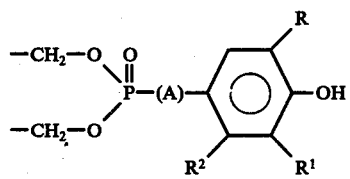

so that this class of compounds has the formula Ie

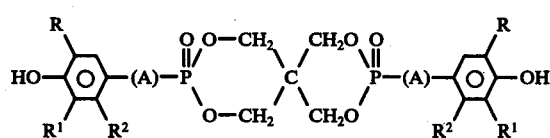

$R^7$ is independently hydrogen, alkyl of 1 to 8 carbon atoms or phenyl,

A is straight or branched lower alkylene chain of 1 to 8 carbon atoms, and n is an integer of 1 to 4.

The R, $R^1$ and $R^2$ groups can be straight or branched lower alkyl groups having 1 to 8 carbon atoms as, for example, methyl, ethyl, propyl, butyl, pentyl, heptyl or octyl. R, $R^1$ and $R^2$ groups can be cycloalkyl of 5 to 6 carbon atoms such as cyclopentyl or cyclohexyl. Preferably R is a branched alkyl group of 3 to 8 carbon atoms such as isopropyl, sec-butyl, tert-butyl, sec- and tert-pentyl, sec- and tert-hexyl, sec- and tert-heptyl or sec- and tert-octyl, and most preferably a tert-bytyl group. $R^1$ and $R^2$ are preferably an alkyl group having 1 to 3 carbon atoms such as methyl, ethyl or isopropyl and most preferably methyl group.

$R^3$ and $R^4$ can be alkyl of 1 to 24 carbon atoms such as methyl, n-butyl, n-octyl, n-dodecyl, n-octadecyl or n-tetracosanyl. Preferably $R^3$ and $R^4$ are alkyl groups of 1 to 18 carbon atoms such as n-dodecyl or n-octadecyl.

$R^3$ and $R^4$ are also phenyl or phenyl substituted with alkyl groups, said alkyl groups having 1 to 18 carbon atoms. The substituents may be methyl, isopropyl, tert-butyl and tert-octyl. Substitution in the ortho or para positions of the phenyl ring is especially preferred. Preferably $R^3$ and $R^4$ are phenyl substituted with alkyl groups having 1 to 12 carbon atoms and most preferably 1 to 8 carbon atoms such as methyl or two tert-butyl groups.

$R^3$ and $R^4$ are also an alkyl group of 1 to 24 carbon atoms substituted with one halogen group, preferably chlorine or bromine. Preferably $R^3$ and $R^4$ are 2-chloroethyl or 2-bromoethyl.

$R^3$ is also alkoxy of 1 to 24 carbon atoms substituted by one halogen group, preferably chlorine or bromine. Preferably $R^3$ is 2-chloroethoxy or 2-bromoethoxy.

The R³ group can also be alkoxy of 1 to 24 carbon atoms such as methoxy, ethoxy, n-dodecyloxy or n-tetracosanyloxy. Preferably R³ is alkoxy of 1 to 18 carbon atoms such as n-octadecyloxy.

R³ is also phenoxy or phenoxy substituted with alkyl groups, said alkyl groups having 1 to 18 carbon atoms, preferably 1 to 8 carbon atoms, such as methyl, tert-butyl or tert-octyl.

R³ is also alkylthioethoxy of 5 to 28 atoms in the chain such as 2-(n-tetracosanylthio)ethoxy, 2-(methylthioethoxy, 2-(n-butylthio)ethoxy, 2-(n-octadecylthio)ethoxy or 2-(n-dodecythio)ethoxy. Preferably R³ is alkylthioethoxy of 6 to 22 atoms in the chain.

R³ is alkylpolyoxyalkeneoxy of 5 to 28 atoms in the chain and having the general structure R°(OCH₂CH₂)$_h$O- where R° is alkyl of 1 to 18 carbon atoms and h is 1 to 3. Preferably R³ is alkylpolyoxyalkeneoxy of 6 to 22 atoms in the chain.

R⁴ can be cycloalkyl of 5 to 6 carbon atoms such as cyclopentyl and cyclohexyl.

R⁴ is also alkylthioethyl of 4 to 27 atoms in the chain such as 2-(methylthio)ethyl, 2-(n-octylthio)ethyl and 2-(n-tetracosanylthio)ethyl. Preferably R⁴ is alkylthioethyl of 5 to 21 atoms in the chain.

Where n is 2, R⁴ is also thiobis-alkylene of 5 to 9 atoms in the chain. Preferably R⁴ is thiodiethylene.

R⁴ is also alkylene of 2 to 12 carbon atoms such as ethylene, tetramethylene, 2,2-dimethylpropylene and dodecamethylene. Preferably R⁴ is alkylene of 2 to 8 carbon atoms and most preferably of 2 to 6 carbon atoms.

R⁴ can be alkyleneoxyalkylene of 5 to 9 atoms in the chain such as oxydiethylene, oxydibutylene and oxydi(1,2-propylene). Preferably R³ is oxydiethylene.

R⁴ can also be polyoxyalkylene of 8 to 101 atoms having the general formula —R°°(OR°°)$_k$— where R°° is a straight or branched lower alkylene of 2 to 4 carbon atoms and k is 2 to 33. R°° is ethylene, 1,2-porpylene,1,2-butylene and tetramethylene. Preferably R⁴ is polyoxyalkylene of 8 to 11 atoms in the chain where R°° is ethylene and k is 2 to 3. Most preferably R⁴ is polyoxyethylene of 8 atoms in the chain.

R⁴ can also be alkylpolyoxyalkylene of 4 to 27 atoms in the chain having the general structure R°(OCH₂CH₂)$_h$— where R° is alkyl of 1 to 18 carbon atoms and h is 1 to 3. Preferably R⁴ is alkylpolyoxyethylene of 5 to 21 atoms in the chain.

Where n is 3 to 4, R⁴ is a polyvalent acyclic or cyclic hydrocarbon radical of 3 to 10 carbon atoms such as 1,2,3-propanetriyl, neopentanetriyl, neopentanetetrayl, 2,2-dimethyl-1,2,2-butanetriyl and 2,2-dimethyl-1,2,2,-pentanetriyl. Preferably R⁴ is a polyvalent acyclic hydrocarbon radical of 3 to 7 carbon atoms.

R⁵ and R⁶ can be independently hydrogen, alkyl of 1 to 12 carbon atoms such as methyl, ethyl, n-propyl, n-hexyl, n-decyl and n-dodecyl. Preferably R⁵ is hydrogen or lower alkyl of 1 to 4 carbon atoms, and R⁶ is lower alkyl of 1 to 4 carbon atoms or the group of formula Ic

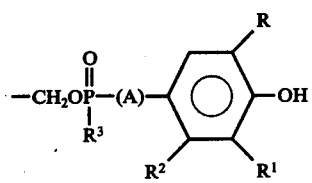

R⁵ and R⁶ together can also preferably represent the group with the formula Id

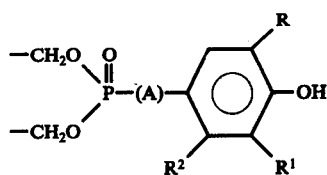

to give spiro[5,5]undecane derivatives of formula Ie.

R⁷ is independently hydrogen, alkyl of 1 to 8 carbon atoms such as methyl, ethyl, n-butyl and n-octyl or phenyl. Preferably R⁷ is hydrogen, methyl or ethyl. Most preferably R⁷ is hydrogen.

A is a straight or branched chain alkylene of 1 to 8 carbon atoms. Preferably A is alkylene of 1 to 4 carbon atoms and most preferably of 1 to 2 carbon atoms such as methylene and ethylene. Of particular importance are the compounds where A is methylene.

A can be a branched alkylene of 2 to 8 carbon atoms such as ethylidene, 1,1-n-butylidene and 1,1-n-octylidene.

n is an integer of 1 to 4, preferably of 1 to 2 and most preferably 1.

Compounds of formula I, where n=1, are made by the reaction of a halide of the formula II

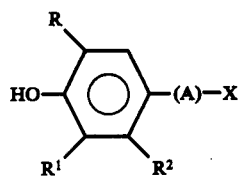

where X = Cl or Br, in turn prepared by conventional halogenomethylation procedures on the corresponding trisubstituted phenol of formula VIII, with a tertiary phosphite of the formula III

or a tertiary phosphonite of the formula IV

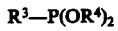

to yield respectively the products where R³ is the same as —OR⁴ or where R³ is an alkyl or aryl directly bonded to phosphorus as defined in formula I above. Substitution of higher aldehydes such as n-butanal and n-octanal for formaldehyde in the preparation of intermediates of formula II lead to compounds where A is 1,1-alkylidene.

Other suitable synthetic routes, where n=1, include the reactions of the compound II with an alkali or metal salt of dialkyl phosphite or diaryl phosphite of the formula V

or a phosphinite of the formula VI

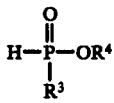

VI in the case, where the $R^3$ is an alkyl or aryl group directly bonded to phosphorus.

2-(Alkylthio)ethyl phosphonates are conveniently made by reacting the corresponding 2-chloroethyl phosphonates with an alkyl mercaptan.

A related method, where $n=1$, and A is methylene or

involves the reaction of compounds of the formula VII with phosphites V or phosphonites VI.

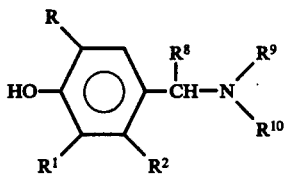

VII where $R^8$ is lower alkyl of 1 to 7 carbon atoms, where $R^9$ and $R^{10}$ are lower alkyl of 1 to 8 carbon atoms and $R^9$ and $R^{10}$ together with N form a morpholine or piperidine ring. Preferably $R^9$ and $R^{10}$ are methyl.

Phosphinates of formula I, where $n=1$, can also be made by the following reaction sequence:

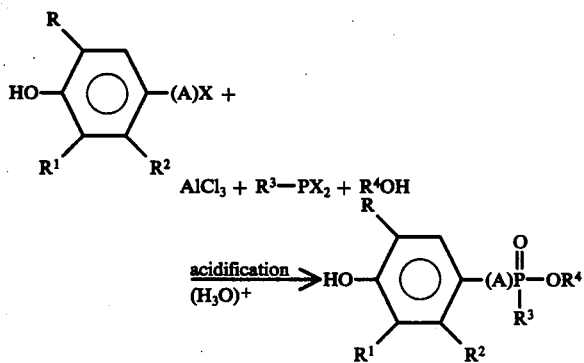

In this latter method, $R^3$ is an alkyl or aryl group defined as above directly bonded to phosphorus.

Compounds where $n=2$ to 4, and where $R^3$ is alkyl or aryl directly bonded to phosphorus, are made by transesterification of the appropriate aryl or alkyl (e.g., phenyl) phosphinate with a polyol or polyhydric phenol.

Compounds of formula Ia and Ib may be conveniently prepared by transesterification of the corresponding lower alkyl phosphonates, preferably the methyl esters, with ethylene glycol, trimethylolethane, trimethylolbutane and pentaerythritol using standard catalysts such as lithium amide, sodium methoxide or lithium hydride.

Compounds of formula Ia and Ib may also be conveniently prepared by reaction of the lower alkyl esters, preferably methyl or ethyl, of the corresponding phosphonate with the alkylene halide such as ethylene dichloride or polyvalent acyclic halide such as pentaerythrityl tetrabromide in sulfolane at elevated temperatures.

Phenols used in the synthesis of the compounds of formula II have the formula VIII

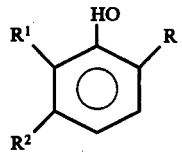

VIII where R, $R^1$ and $R^2$ are as previously defined. Of particular interest are those in which $R^1$ and $R^2$ are methyl since these are readily prepared from commercially available 2,3-xylenol. Thus, for example, the preparation of 2,3-dimethyl-6-tert.-butylphenol is described by G. Parc in Revue De L'Institut Francais Du Petrole, Vol. XV, page 693 (1960).

Particularly interesting phenols are those in which R and $R^1$ are either isopropyl or t-butyl and $R^2$ is methyl. The preparation of 2,6-diisopropyl-m-cresol and 2,6-di-tert.-butyl-m-cresol is described in Japanese patent application 70 15,491 issued May 30, 1971.

The trialkylsubstituted hydroxyphenylalkanephosphonates and phosphinates of this invention are stabilizers of organic material normally subject to thermal and oxidative deterioration. Materials which are thus stabilized include synthetic organic polymeric substances such as vinyl resins formed from the polymerization of vinyl halides or from the copolymerization of vinyl halides with unsaturated polymerizable compounds, e.g., vinyl esters, $\alpha,\beta$-unsaturated ketones, $\alpha,\beta$-unsaturated aldehydes and unsaturated hydrocarbons such as butadienes and styrene; poly-$\alpha$-olefins such as polyethylene, polypropylene, polybutylene including copolymers of $\alpha$-olefins such as ethylene/propylene copolymer; dienes such as polybutadiene, polyisoprene, and the like, including copolymers with other monomers; polyurethanes and polyamides such as polyhexamethylene adipamide and polycaprolactam; polyesters such as polyethylene terephthalates; polycarbonates; polyesters such as polybutylene terephthalate; polyacetal; polystyrene, polyethylene oxide; and copolymers such as those of high impact polystyrene containing copolymers of butadiene and styrene and those formed by the copolymerization of acrylonitrile, butadiene and/or styrene; natural and synthetic rubbers such as ethylene/propylene/diene copolymer (EPDM) and chlorinated rubber; and polyphenylene oxide and copolymers.

Other materials which can be stabilized by the compounds of the present invention include lubricating oil of the aliphatic ester type, i.e., di(2-ethylhexyl) azelate, and other synthetic ester lubricants, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., $\beta$-methoxyethylene glycol, methoxytriethylene glycol, triethylene glycol, octaethylene glycol, dibutylene glycol, dipropylene glycol and the like.

The substrates of particular importance are olefin polymers such as polyethylene and polypropylene.

Polypropylene is especially well stabilized by the compounds of this invention.

In general, the stabilizers of this invention are employed from 0.01 to about 5% by weight of the stabilized composition, although this will vary with the particular substrate and application. An advantageous range is from about 0.05 to about 2% and especially from 0.1 to about 1%.

For addition to polymeric substrates, the stabilizers can be blended before polymerization or after polymerization, during the usual processing operations, for example, by hot-milling, the composition then being extruded, pressed, or the like into films, fibers, filaments, hollow spheres and the like. The heat stabilizing properties of these compounds advantageously stabilize the polymer against degradation during such processing at the high temperature generally encountered. The stabilizers can also be dissolved in suitable solvents and sprayed on the surface of films, fabrics, filaments or the like to provide effective stabilization.

These compounds can also be used in combination with other additives such as sulfur-containing esters, e.g., distearyl β-thiodipropionate (DSTDP), dilauryl β-thiodipropionate (DLTDP), in an amount of from 0.01 to 2% by weight of the organic material, and the like, pourpoint depressants, corrosion and rust inhibitors, dispersing agents, emulsifiers, antifoaming agents, carbon black, accelerators and other chemicals used in rubber compounding, plasticizers, color stabilizers, fillers, dyesites, surface active agents di- and -tri-alkyl- and alkylphenylphosphites, heat stabilizers, ultraviolet ligh stabilizers, antiozonates, dyes, pigments, metal chelating agents, and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

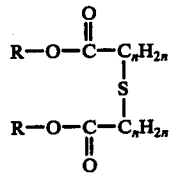

wherein R is an alkyl group having from 6 to 24 carbon atoms; and n is an integer from 1 to 6. Especially useful compounds of this type are dilauryl β-thiodipropionate and distearyl β-thiodipropionate. The above co-stabilizers are used in the amount of from 0.01 to 2% by weight of the organic material, and preferably from 0.1 to 1%.

In addition to the above noted additives that can be employed in combination with the compounds of this invention, it is often especially advantageous to employ also light stabilizers. The light stabilizers are used in the amount of from 0.01 1 to 5% by weight of the organic material, and preferably from 0.1 to 1%. Illustrative examples of light stabilizers are listed below.

UV ABSORBERS AND LIGHT PROTECTION AGENTS 2-(2'-hydroxyphenyl)-benztriazoles, such as for example, the 5'-methyl-, 3',5'-di-tert.-butyl-,5'-tert.-butyl-,5'-(1,1,3,3-tetramethyl-butyl)-, 5-chloro-3', 5'-di-tert.-butyl-, 5-chloro-3'-tert.-butyl-5'-methyl-, 3'-sec.-butyl-5'-tert.-butyl-, 3'-{α-methyl-benzyl}-5'-methyl-, 3'-{α-methylbenzyl}-5'-methyl-5-chloro-, 4'-hydroxy-, 4'-methoxy-, 4'-octoxy-, 3',5'-di-tert.-amyl-, 3'methyl-5'-carbomethoxyethyl- or 5-chloro-3',5'-di-tert.-amyl-derivatives.

2,4-Bis-(2'-hydroxyphenyl)-6-alkyl-s-triazines, such as, for example, the 6-ethyl-, 6-undecyl- or 6-heptadecyl-derivatives.

2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy or 2'-hydroxy-4,4'-dimethoxy-derivatives.

1,3-Bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octoxy-benzoyl)-benzene and 1,3-bis-(2'-hydroxy-4'-dodecyloxy-benzoyl)-benzene.

Esters of optionally substituted benzoic acids, such as, for example, phenyl salicylate, octylphenyl salicylate, di-benzoylresorcinol, bis-(4-tert.-butylbenzoyl)-resorcinol, benzoyl-resorcinol, 3,5-di-tert.-butyl-4-hydroxybenzoic acid 2,4-di-tert.-butyl-phenyl ester, octadecyl ester or 2-methyl-4,6-di-tert.-butylphenyl ester.

Acrylates, such as, for example, α-cyanoβ,β-diphenyl-acrylic acid ethyl ester or isooctyl ester α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.

Nickel compounds, such as, for example, nickel complexes of 2,2'-thio-bis-4-(1,1,3,3-tetramethylbutyl)-phenol such as the 1:1 and 1:2 complex, optionally with other ligands such as n-butylamine, triethanolamine or N-cyclohexyl-diethanolamine; nickel complexes of bis-{2-hydroxy-4-(1,1,3,3-tetramethylbutyl)-phenyl}-sulphone, such as the 2:1 complex optionally with other ligands such as 2-ethyl-caproic acid; nickel dibutyldithiocarbamate, nickel salts of 4-hydroxy-3,5-di-tert.-butyl-benzylphosphonic acid monoalkyl esters, such as the methyl, ethyl or butyl ester, the nickel complex of (2-hydroxy-4-methyl-phenyl)-undecyl-ketonoxime and nickel 3,5-di-tert.-butyl-4-hydroxybenzoate.

Oxalic acid diamides, such as, for example, 4,4'-dioctyloxyoxanilide, 2,2'-dioctyloxy-5,5'-di-tert.-butyl-oxanilide, 2,2'-di-dodecyloxy-5,5'-di-tert.-butyloxanilide, 2-ethoxy-5-tertiarybutyl-2'-ethyl-oxanilide, 2-ethoxy-2'ethyl-oxanilide, N,N'-bis-(3-dimethylamino-propyl) oxalamide, mixtures of o- and p-methoxy and o- and p-ethoxy-di-substituted oxanilides and mixtures of 2-ethoxy-5-tert.-butyl-2'-ethyl-oxanilide with 2-ethoxy2'-ethyl-5,4'-di-tert.-butyl-oxanilide.

Sterically hindered amines, such as, for example, 4-benzoyloxy-2,2,6,6-tetramethylpiperidine, 4-stearoyloxy-2,2,6,6-tetramethylpiperidine, bis(2,2,6,6-tetramethylpiperidyl)-sebacate and 3-n-octyl-7,7,9,9-tetramethyl-1,3-triaza-spiro[4,5]decane-2,4-dione.

The hindered hydroxyphenylalkanephosphonates and phosphinates of this invention not only have superior stabilizing properties, but exhibit resistance to gas fading in polymeric substrates such as polypropylene multifilament knitted cloth to a high degree not shown by other antioxidants. In addition, the stabilizers of this invention confer superior processing stability to polymers, such as polypropylene as well as being extraction resistant. This combination of properties is particularly important for textiles fabricated for synthetic polymers.

For exemplification purposes only listed below are compounds of this invention which are useful as stabilizers as discussed above.

dimethyl 5-t-butyl-2,3-dimethyl-4-hydroxybenzylphosphonate
di-n-octyl 5-isopropyl-2,3-dimethyl-4-hydroxybenzylphosphonate
di-n-octadecyl 5-t-butyl-2,3-dimethyl-4-hydroxybenzylphosphonate
diethyl 5-t-butyl-2,3-dimethyl-4-hydroxybenzylphosphonate
di-n-butyl 5-t-butyl-2,3-dimethyl-4-hydroxybenzylphosphonate
di-n-dodecyl 5-t-butyl-2,3-dimethyl-4-hydroxybenzylphosphonate
di-n-dodecyl 5-t-octyl-2,3-dimethyl-4-hydroxybenzylphosphonate
di-n-octadecyl(2-t-butyl-1-hydroxy-5,6,7,8-tetrahydronaphthyl-4)-methanephosphonate
diphenyl 2,3,5-triisopropyl-4-hydroxybenzylphosphonate
di-n-octadecyl 5-cyclohexyl-2,3-dimethyl-4-hydroxybenzylphosphonate
bis-(2-chloroethyl) 5-t-butyl-4-hydroxy-2,3-dimethylbenzylphosphonate
bis-[2-(n-octadecylthio)ethyl] 5-t-butyl-4-hydroxy-2,3-dimethylbenzylphosphonate
bis-(1,3-dimethylphenyl) 5-t-butyl-4-hydroxy-2,3-diethylbenzylphosphonate
bis-[2-(n-octylthio)ethyl] 5-t-butyl-4-hydroxy-2,3-dimethylbenzylphosphonate
n-octadecyl (5-tert.-butyl-2,3-dimethyl-4-hydroxybenzyl)ethanephosphinate
n-dodecyl (5-tert.-octyl-2,3-dimethyl-4-hydroxybenzyl)benzenephosphinate
methyl (5-tert.-butyl-2,3-dimethyl-4-hydroxybenzyl)benzenephosphinate
phenyl (5-tert.-butyl-2,3-dimethyl-4-hydroxybenzyl)benzenephosphinate
p-tert.-octylphenyl(5-tert.-butyl-2,3-dimethyl-4-hydroxybenzyl)methanephosphinate
2,2-dimethylpropylene bis[(5-tert.-butyl-2,3-dimethyl-4-hydroxybenzyl)benzenephosphinate]
thiodiethylene bis{(5-tert.-butyl-2,3-dimethyl-4-hydroxybenzyl)benzenephosphinate}
di-n-octadecyl 2-(5-tert.-butyl-2,3-dimethylphenyl)ethanephosphonate
di-n-octyl 3-(5-tert.-butyl-2,3-dimethylphenyl)propanephosphonate
neopentanetriyl tris[(5-tert.-butyl-2,3-dimethyl-4-hydroxybenzyl)benzenephosphinate]
neopentanetetrayl tetrakis[(5-tert.-butyl-2,3-dimethyl-4-hydroxybenzyl)benzenephosphinate]
2-(5-tert.-octyl-2,3-dimethyl-4-hydroxybenzyl)-2-oxo-1,3-dioxa-2-phosphacyclopentane
3,9-bis(2-tert.-butyl-1-hydroxy-5,6,7,8-tetrahydronaphthyl-4)methane-3,9-dioxo-2,4,8,10-tetraoxa-3,9-diphosphaspiro[5,5]undecane
2-(5-tert.-butyl-2,3-dimethyl-4-hydroxybenzyl)-2-oxo-1,3-dioxa-2-phosphacyclohexane
2-(5-tert.-butyl-2,3-dimethyl-4-hydroxybenzyl)-2-oxo-1,3-dioxa-2-phospha-5,5-dimethylcyclohexane
ethyl 2-(5-tert.-butyl-2,3-dimethyl-4-hydroxybenzyl)-2-oxo-1,3-dioxa-2-phospha-5-ethylcyclohex-5-ylmethyl 5-tert.-butyl-2,3-dimethyl-4-hydroxybenzylphosphonate The following examples are illustrative of the invention, but are not meant to limit the scope of same. In said examples, parts are by weight unless otherwise indicated and the relationship between parts by weight and parts by volume is as that between grams and cubic centimeters. The temperatures are in degrees centigrade.

EXAMPLE 1

6-tert.-Butyl-2,3-dimethyl-4-(dimethylaminomethyl)-phenol

To 142.4 grams of 6-tert.-butyl-2,3-dimethylphenol dissolved in 270 ml of toluene was added 144.4 grams of a 25% aqueous solution of dimethylamine at about room temperature. 65.7 grams of 36.5% aqueous formaldehyde was then added over a ten minute period to the reaction mixture initially at 15°, the temperature rising to 30° at the end of the addition. The reaction mixture was then warmed to 40° for 3 hours and finally heated at reflux (85°) for two hours. The reaction was diluted with about 1 liter of ether and the aqueous layer separated, the upper ether layer being washed three times with water. After drying over sodium sulfate, the organic phase was stripped to dryness at reduced pressures yielding 176.3 grams of crude product. The crude product was crystallized from heptane, yielding white crystals melting at 101° to 104°.

EXAMPLE 2

6-tert.-Octyl-2,3-dimethyl-4-(dimethylaminomethyl)-phenol

This compound was made in substantially the same manner as described in Example 1 by substituting 6-tert.-octyl-2,3-dimethylphenol for the 6-tert.-butyl analog. After trituration from n-hexane, the desired product was obtained as white crystals, melting at 130° to 132° C.

EXAMPLE 3

2-tert.-Butyl-4-(dimethylaminomethyl)-5,6,7,8-tetrahydro-1-naphthol

This compound was made in substantially the same manner as described in Example 1 by substituting 2-tert.-butyl-5,6,7,8-tetrahydro-1-naphthol for 6-tert.-butyl-2,3-dimethylphenol. After crystallization from acetonitrile the desired compound was obtained as white crystals melting at 95° to 105° C with decomposition.

EXAMPLE 4

Dimethyl 5-tert.-butyl-2,3-dimethyl-4-hydroxybenzylphosphonate 16.4 grams of the compound of Example 1 and 13.6 grams of dimethyl phosphite were dissolved in 25 ml of dry N,N-dimethylformamide, warmed with stirring in a stream of nitrogen and heated to 39° when dimethylamine was observed to evolve. The reaction temperature was raised to 60° over a period of 3 hours and 20 minutes, the temperature being held at this same temperature for an additional 16 hours. The reaction mixture was poured into about 150 ml of water to precipitate the product as a solid. The solid was filtered and taken up in benzene, the benzene solution being washed successively with water, 20 ml of 2N aqueous sodium hydroxide, again with water until the wash water was neutral, then with aqueous saturated sodium bicarbonate, water, dilute aqueous hydrochloric acid and finally with water until the wash water was in the range of pH 5 to 6. After drying with anhydrous sodium sulfate and removing the drying agent by filtration, the clear filtrate was evaporated at reduced pressure to remove the solvent, the product being isolated as a residual solid. After crystallization from acetonitrile the desired compound was isolated as white crystals melting at 154° to 158° C (Compound 1).

EXAMPLE 5

Di-n-octadecyl 5-tert.-butyl-2,3-dimethyl-4-hydroxybenzylphosphonate

To 37.6 grams of the compound of Example 1 and 94 grams of di-n-octadecyl phosphite dissolved in 100 ml of dry N,N-dimethylformamide at 55° to 60° was added 2.16 grams of lithium amide and the reaction temperature raised to 106° and kept at 105° to 107° for 1¼ hours, the evolved dimethylamine being swept out of the reaction mixture by a stream of nitrogen. The reaction mixture was dissolved in about one liter of a solvent mixture of toluene, chloroform and benzene containing 6 grams of acetic acid, filtered free of some insoluble by-product. The clear filtrate was washed successively with water, 6N aqueous hydrochloric acid, and water until the wash water was in the pH range of 5 to 6. The solvent solution of the product was dried over anhydrous sodium sulfate. After removing the drying agent by filtration, the clear filtrate was freed of solvent by distillation at reduced pressures yielding a solid residue which afforded the desired compound as white crystals at 91° to 93° after crystallization from isopropanol (Compound 2).

Other dialkyl 3-tert.-butyl-5,6-dimethyl-4-hydroxybenzylphosphonates (Table I) were made by a similar procedure as described in Example 5.

TABLE I

Other Dialkyl 5-tert.-butyl-2,3-dimethyl-4-hydroxybenzylphosphonates

| Compound No. | $R^3$ | $R^4$ | M.P. ° C |
|---|---|---|---|
| 3 | $-OC_2H_5$ | $C_2H_5-$ | 170-172.5 |
| 4 | $-O-n-C_4H_9$ | $n-C_4H_9-$ | 98-101 |
| 5 | $-O-n-C_{12}H_{25}$ | $n-C_{12}H_{25}-$ | 66-69 |

EXAMPLE 6

Di-n-octadecyl 5-tert.-octyl-2,3-dimethyl-4-hydroxybenzylphosphonate

This compound was made in a similar manner as Example 5 by substituting 6-tert.-octyl-2,3-dimethyl-4-(dimethylaminomethyl)phenol (Example 2) for the tert.-butyl analog. After crystallization from acetone, the title compound was obtained as white crystals melting at 64° to 66° C (Compound 6).

EXAMPLE 7

Di-n-dodecyl 5-tert.-octyl-2,3-dimethyl-4-hydroxybenzylphosphonate

This compound was made in a similar manner as Example 5 by reacting 6-tert.-octyl-2,3-dimethyl-4-(dimethylaminomethyl)phenol (Example 2) with di-n-dodecyl phosphite. After trituration with acetonitrile, the desired compound is obtained as white crystals melting at 36° to 40° C (Compound 7).

EXAMPLE 8

Di-n-octadedyl (2-tert.-butyl-1-hydroxy5,6,7,8-tetrahydronaphthyl-4)methanephosphonate This compound was made in a similar manner as Example 5 by substituting 2-tert.-butyl-4-dimethylaminomethyl-5,6,7,8-tetrahydro-1-naphthol for 6-tert.-butyl-2,3-dimethyl-4-(dimethylaminomethyl)-phenol. After crystallization from isopropanol, the desired compound is obtained as white crystals melting at 75° to 77° C (Compound 8).

EXAMPLE 9

5-tert.-Butyl-2,3-dimethyl-4-hydroxybenzyl chloride

30grams of 6-tert.-butyl-2,3-dimethylphenol dissolved in 100 ml of toluene was added to 2.7 ml of concentrated hydrochloric acid containing 3.3 ml of concentrated sulfuric acid at 5° to 10° C. 26 grams of methylal was added dropwise to the above vigorously stirred dispersion over a period of about 15 minutes After this the reaction mixture was heated at 36° to 37° for two hours while bubbling anhydrous gaseous hydrogen chloride through the reaction mixture. The reaction temperature was allowed to drop to 27° during the following two hours while continuing to bubble anhydrous hydrogen chloride through the reaction mixture. The acidic aqueous phase was separated from the reaction mixture after being extracted with toluene. The combined toluene phases were washed well with cold water and dried over anhydrous sodium sulfate. After filtering free of drying agent, the clear filtrate was freed of solvent by distillation at reduced pressures the resulting residue being crystallized from petroleum ether yielding the desired compound in the form of light yellow crystals melting at 92° to 95° C.

EXAMPLE 10

Bis-(2-chloroethyl) 5-tert.-butyl-2,3dimethyl-4-hydroxybenzylphosphonate 13.45 tris-(2-chloroethyl) phosphite and 11.55 grams of the compound of Example 9 dissolved in 50 ml of dry xylene were mixed together and heated at 65° for 3 hours and then at 110° to 115° C for 2 ½ hours during which 1,2-dichloroethane distilled out of the reaction mixture and was collected in a trap. The reaction mixture was freed of solvent at reduced pressure, the resulting solid was triturated with petroleum ether and then recrystallized successively from a solvent mixture of benzene-hexane and then from toluene, yielding the desired product as white crystals melting at 133° to 135° C (Compound 9).

EXAMPLE 11

Bis[2-(n-octadecylthio)ethyl]5-tert.-butyl2,3-dimethyl-4-hydroxylbenzylphosphonate To a sodium dispersion of 0.72 grams of sodium metal in 150 ml of xylene at 60°, was added dropwise a solution of 9.0 grams of n-octadecyl mercptan dissolved in 30 ml of xylene. The reaction mixture was kept at 60° for 45 minutes and then at 100° for 15 minutes at the end of which time the sodium was completely reacted. A solution of 5.96 grams of the compound of Example 10 in 70 ml of xylene was added rapidly dropwise to the reaction mixture at room temperature, following which the reaction mixture was first heated at 50° to 55° for 2 hours, then at 120° for 5 hours and finally at 137° for 3 hours. The cooled reaction mixture was successively washed with 3N hydrochloric acid, water, 2N aqueous sodium hydroxide and finally with water until the wash water was neutral. The organic phase was then dried over anhydrous sodium sulfate. After removing the drying agent by filtration and the solvent by distillation at reduced pressures, the turbid solution of the residue in nitromethaneacetone was clarified by filtration through filtercel and allowed to crystallize by cooling, yielding a crystalline precipitate. This precipitate was crystallized successively from a mixture of nitromethane-acetone, n-heptane and isopropanol yielding the desired compound as white crystals melting at 71° to 73° C (Compound 10).

EXAMPLE 12 n-Dodecyl (5-tert.-butyl-2,3-dimethyl-4-hydroxybenzyl)benzenephosphinate

A solution of 14.7 grams of aluminum chloride (0.110 mole) in 50 ml of nitromethane is added dropwise over a period of 15 minutes to a solution of 22.6 grams of 5-tert.-butyl-2,3-dimethyl-4-hydroxybenzyl chloride (0.100 mole) and 18.7 grams of dichlorophenylphosphine (0.105 mole) in 50 ml of nitromethane at $-15°$ to $-10°$ C, the reaction mixture then being stirred at the same temperature for about 1 hour. 41.1 grams of n-dodecanol (0.220 mole) is then added dropwise at $-10°$ to $+10°$ C, stirring at 20° to 30° C being continued for about 2 hours. After treatment with water at 20° C, the reaction dispersion is extracted with 300 ml ether, the extracts being washed with 100 ml of water containing 20 ml of concentrated hydrochloric acid and water again, the ether layer being dried over sodium sulfate. The product is recovered after removal of the ether by distillation.

EXAMPLE 13 n-Octadecyl (5-tert.-butyl-2,3-dimethyl4-hydroxybenzyl)ethanephosphonate

This compound is prepared in similar manner to the procedure described in Example 12 by substituting dichloroethylphosphine and n-octadecanol for dichlorophenylphosphine and n-dodecanol respectively.

EXAMPLE 14

Methyl (5-tert.-butyl-2,3-dimethyl-4hydroxybenzyl)benzenephosphinate

This compound is prepared by an analogous method to that described in Example 12 by substituting methanol for n-dodecanol.

EXAMPLE 15

3,9-Bis-(5-tert.-butyl-2,3-dimethyl-4-hydroxybenzyl)-3,9-dioxo-2,4,8,10-tetraoxa3,9-diphosphaspiro[5,5]undecane 16.4 grams of diethyl 5-tert-butyl-2,3-dimethyl4-hydroxybenzylphosphonate (0.05 moles) and 9.7 grams of pentaerythrityl tetrabromide (0.025 moles) were dissolved together in 25 ml of sulfolane and heated at 200° to 205° C for 8 hours with 10.7 grams of evolved ethyl bromide being collected (theory is 10.8 grams). The reaction mixture was dissolved in 100 ml of chloroform and successively washed with water, 1 normal aqueous sodium hydroxide and finally with saturated aqueous sodium chloride solution until the pH of the wash water was neutral. After drying over sodium sulfate and removal of the chloroform solvent at reduced pressure, the crude product was isolated as a glassy residue. This was powdered and triturated with 100 ml of toluene to yield a white crystalline solid which after successive recrystallizations from nitromethane and then ethanol yielded white crystals melting at 255°–258° C after drying (Compound 11).

Unstabilized polypropylene powder (Hercules Profax 6501) was thoroughly blended with 0.2% by weight of the indicated stabilizer compound. Also prepared were samples of polypropylene containing 0.1% by weight of the same stabilizer and 0.3% by weight of DSTDP (distearyl β-thiodipropionate). The blended materials were then milled on a two-roll mill at 182° C for 10 minutes, after which time the stabilized polypropylene was sheeted from the mill and allowed to cool.

The milled polypropylene sheets were then cut into pieces and pressed for 7 minutes on a hydraulic press at 218° C, 19.25 Kg/cm² pressure. The resulting plaques of 0.635 mm thickness were tested for resistance to accelerated aging in a forced draft oven at 150° C.

When the plaques showed the first signs of decomposition (e.g., cracking or brown edges) they were considered to have failed. The results are shown in Table II below.

TABLE II

OVEN AGING OF POLYPROPYLENE

| Ex. No. | Percent Stabilizer | Hours to Failure |
|---|---|---|
| 16 | 0.2% Compound 1 | < 20 |
| 17 | 0.1% Compound 1 + 0.3% DSTDP | 330 |
| 18 | 0.2% Compound 4 | < 20 |
| 19 | 0.1% Compound 4 + 0.3% DSTDP | 275 |
| 20 | 0.2% Compound 5 | 85 |
| 21 | 0.1% Compound 5 + 0.3% DSTDP | 2040 |
| 22 | 0.2% Compound 2 | 110 |
| 23 | 0.1% Compound 2 + 0.3% DSTDP | 2580 |
| 24 | 0.2% Compound 6 | 20 |
| 25 | 0.1% Compound 6 + 0.3% DSTDP | 1485 |
| 26 | 0.2% Compound 7 | 20 |
| 27 | 0.1% Compound 7 + 0.3% DSTDP | 1580 |
| 28 | 0.2% Compound 8 | 165 |
| 29 | 0.1% Compound 8 + 0.3% DSTDP | 920 |
| 30 | 0.2% Compound 3 | < 20 |
| 31 | 0.1% Compound 3 + 0.3% DSTDP | 275 |
| 32 | 0.2% Compound 9 | < 20 |
| 33 | 0.1% Compound 9 + 0.3% DSTDP | 135 |
| 34 | 0.2% Compound 10 | 105 |
| 35 | 0.1% Compound 10 + 0.3% DSTDP | 280 |

TABLE II-continued
OVEN AGING OF POLYPROPYLENE

| Ex. No. | Percent Stabilizer | Hours to Failure |
| --- | --- | --- |
| 36 | No Stabilizer | 3 |

EXAMPLE 37

Pellets (500 g) of unstabilized nylon-6,6 (Zytel 101, DuPont) are placed in a Kitchen Aid Mixer. With mixing a solution of 0.5% (based on the weight of nylon) of 3,9-bis(5-tert.-butyl-2,3-dimethyl-4-hydroxybenzyl)-3,9-dioxo-2,4,8,10-tetraoxa-3,9-diphosphaspiro[5,5]undecane in 20 ml of methylene chloride is added slowly. Sodium hypophosphite (0.5 gm 0.1%) is dissolved in 20 ml water and added slowly with mixing to the nylon pellets after the antioxidant solution has been added and most of the methylene chloride has evaporated. The stabilized pellets are dried at 80° C at <<1 mm Hg. for 4 hours.

The polyamide formulation is extruded at 315.6° C through a 0.635 cm die into a rod which is water cooled and chopped into pellets. A 1.905 cm Brabender extruder, equipped with a nylon screw, is used. The pellets are dried at 80° C at <1 mm for 4 hours.

The dried pellets are compression molded into 0.127 mm thick film by pressing at 290° C for 4 minutes at 57.75 Kg/cm$^2$. The films are oven aged at 150° C in a forced draft oven and samples are removed periodically. The specific viscosity of the samples are determined using a 1% formic acid solution at 25° C. The sample stabilized with the above noted stabilizer required longer aging time to reduce its viscosity by one-half than the unstabilized sample.

EXAMPLE 38

Unstabilized high impact polystyrene resin is dry blended with 0.05% by weight of the resin of di-n-octadecyl 5-tert.-butyl-2,3-dimethyl-4-hydroxybenzylphosphonate. The resin is then extrusion compounded on a 2.54 cm 24/1=L/D extruder, melt temperature 260° C and pressed for 7 minutes at a temperature of 163° C and a pressure of 140 Kg/cm$^2$ into a sheet of uniform thickness of 2.54 mm. The sheets are then cut into plaques of 5.08 cm × 5.08 cm. The plaques are then oven aged at 80° C and color measurements made periodically using a Hunter Color Difference Meter Model D25. The polystyrene samples stabilized with the above stabilizer develops the undesirable yellow discoloration substantially later than the time that such discoloration occurred in the unstabilized samples.

EXAMPLE 39

Unstabilized linear polyethylene (HiFax 4401) is solvent blended in methylene chloride with 0.5% by weight of the substrate of di-n-dodecyl 5-tert.-butyl-2,3-dimethyl-4-hydroxybenzylphosphonate and then vacuum dried. The resin is then extruded at 232.2° C as described in Example 38. The melt flow rate of a sample of the resin is determined after each extrusion according to ASTM test D-1238. Polyethylene stabilized with the above compound is found to undergo less change in the melt flow rate than the unstabilized polyethylene.

EXAMPLE 40

A quantity of SBR emulsion containing 100 g of rubber (500 ml of a 20% SBR emulsion obtained commercially from Texas U.S., as Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 1.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1 mm) at 40° to 45° C.

The dried rubber (25 g) is heated under nitrogen at 125° C in a Brabender mixer and to this is added with mixing 0.1% bis[2-(n-octadecylthio)ethyl] 5-tert.-butyl-4-hydroxy-2,3-dimethylbenzylphosphonate.

Portions of the rubber are oven aged at 100° C. At various intervals gel content is determined on the rubber. The rubber stabilized with the above compound shows much less gel formation than the unstabilized sample.

EXAMPLE 41

To 50 g of polyacetal resin containing 0.1% of an acid scavenger, dicyandiamide, is added 0.2% by weight of n-octadecyl (5-tert.-butyl-2,3-dimethyl-4-hydroxybenzyl)-ethanephosphonate and milled for 7 minutes at 200° C in a Brabender Plastirecorder. The milled formulation is subsequently pressed into a 1.016 mm sheet at 215° C at 245 Kg/cm$^2$ for 90 seconds then cooled quickly in a cold press at 24.5 Kg/cm$^2$. The stabilized sheets are then remolded for 2 minutes at contact pressure and for 3 minutes at 21 Kg/cm$^2$ at 215° C to give plaques 3.81 cm × 5.715 cm × 3.175 mm.

The plaques are aged in the oven at 60° C and the weight loss of the specimen is determined periodically until a 4% weight loss is reached. The stabilized sample takes a much longer time to reach this 4% weight loss than does the unstabilized sample.

EXAMPLE 42

Unstabilized thoroughly dried polyethylene terephthalate chips are dry blended with 1.0% of di-n-octadecyl 5-tert.-octyl-2,3-dimethyl-4-hydroxybenzylphosphonate. 60/10 denier multifilament is melt spun at a melt temperature of 290° C and cold oriented 3 to 1. The oriented fibers are wound into skeins and oven aged at 140° C. The stabilized material exhibits greater retention of tensile strength after 24 hours than the unstabilized material.

EXAMPLE 43

A stabilized high temperature lubricating oil is prepared by incorporating 0.05% by weight of di-n-octadecyl (2-tert.-butyl-1-hydroxy-5,6,7,8-tetra-hydronaphthyl-4)methanephosphonate to the lubricant which comprises diisoamyl adipate. The stabilized composition is compared with the unstabilized lubricant by heating at 175° C in the presence of air and metallic catalysts according to the test method described in Military Specification Mil-I-7808c. After 72 hours, the blank containing

What is claimed is:

1. A composition of matter comprising a synthetic organic polymer and,
   a. from 0.01 to 5% by weight of a stabilizing compound of the formula

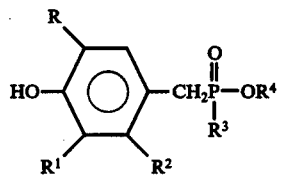

wherein R is alkyl of 4 to 8 carbon atoms, $R^1$ and $R^2$ are methyl or together are a butylene chain which, together with the phenyl group, forms a tetrahydronaphthyl group, $R^3$ is alkoxy of 12 to 24 carbon atoms, and $R^4$ is alkyl of 12 to 24 carbon atoms, and
   b. from 0.01 to 2% by weight of a thio co-stabilizer having the formula

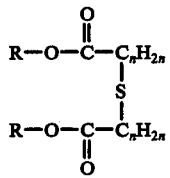

wherein R is alkyl of 6 to 24 carbon atoms and $n$ is 1 to 6.

2. A composition according to claim 1 wherein the stabilizing compound is di-n-octadecyl 5-tert-butyl-2,3-dimethyl-4-hydroxybenzylphosphonate.

3. A composition according to claim 1 wherein the stabilizing compound is di-n-dodecyl 5-tert-butyl-2,3-dimethyl-4-hydroxybenzylphosphonate.

4. A composition according to claim 1 wherein the stabilizing compound is di-n-octadecyl 5-tert-octyl-2,3-dimethyl-4-hydroxybenzylphosphonate 5. A composition according to claim 1 wherein the stabilizing compound is di-n-dodecyl 5-tert-octyl-2,3-dimethyl-4-hydroxybenzylphosphonate.

6. A composition according to claim 1 wherein the stabilizing compound is di-n-octadecyl (2-tert-butyl-1-hydroxy-5,6,7,8-tetrahydronaphthyl-4)methanephosphonate.

7. A composition of claim 1 wherein the synthetic organic polymer is polyolefin.

* * * * *